(12) United States Patent
Salam et al.

(10) Patent No.: US 10,231,458 B1
(45) Date of Patent: Mar. 19, 2019

(54) NANOCOMPOSITE AND A METHOD OF MAKING THE SAME

(71) Applicant: King Abdulaziz University, Jeddah (SA)

(72) Inventors: Mohamed Abdel Salam, Ottawa (CA); Abdullah Yousef Obaid, Jeddah (SA); Reda Mohamed El-Shishtawy, Giza (EG); Saleh Ahmed Mohamed, Giza (EG)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/723,753

(22) Filed: Oct. 3, 2017

(51) Int. Cl.
    *A01N 59/16* (2006.01)
    *A01N 25/26* (2006.01)
    *A01N 25/10* (2006.01)

(52) U.S. Cl.
    CPC ............ *A01N 59/16* (2013.01); *A01N 25/10* (2013.01); *A01N 25/26* (2013.01)

(58) Field of Classification Search
    None
    See application file for complete search history.

(56) References Cited

U.S. PATENT DOCUMENTS

| 8,871,300 | B2 | 10/2014 | Guo et al. | |
|---|---|---|---|---|
| 2008/0194736 | A1* | 8/2008 | Lu | B82Y 30/00 524/35 |
| 2014/0364529 | A1 | 12/2014 | Park et al. | |

FOREIGN PATENT DOCUMENTS

| CN | 105753115 A | 7/2016 |
|---|---|---|
| JP | 2014-67713 A | 4/2014 |

OTHER PUBLICATIONS

Chen et al., Carbon Nanotube and Polypyrrole Composites:Coating and Doping, Adv. Mater. 2000, 12, No. 7 (Year: 2000).*
Balint et al., Conductive polymers: Towards a smart biomaterial for tissue engineering, Acta Biomaterialia 10 (2014) 2341-2353 (Year: 2014).*
Omastova et al., Polypyrrole/silver composites prepared by single-step synthesis, Synthetic Metals 166 (2013) 57-62 (Year: 2013).*
Wang et al., Uniform silver/polypyrrole core-shell nanoparticles synthesized by hydrothermal reaction, Materials Chemistry and Physics 102 (2007) 255-259 (Year: 2007).*
Zhou et al., Functionalized Single Wall Carbon Nanotubes Treated with Pyrrole for Electrochemical Supercapacitor Membranes, Chem. Mater. 2005, 17, 1997-2002 (Year: 2005).*
Hongyu Mi, et al., "Ag-loaded polypyrrole/carbon nanotube: one-step in situ polymerization and improved capacitance", Advanced Materials Research, vol. 531, 2012. pp. 35-38.
Jiangang Wang, et al., "Functionalization of MWCNTs with silver nanoparticles decorated polypyrrole and their application in anti-static and thermal conductive epoxy matrix nanocomposite", RSC Advances, Issue 38, 2016, 2 pages (Abstract only).

* cited by examiner

*Primary Examiner* — Jennifer A Berrios
(74) *Attorney, Agent, or Firm* — Oblon, McClelland, Maier & Neustadt, L.L.P.

(57) ABSTRACT

A nanocomposite that includes a core containing silver nanoparticles, and a shell that includes polypyrrole and carbon nanotubes, wherein the polypyrrole covers at least a portion of the carbon nanotubes, and wherein the shell covers at least a portion of the core and a method of making the nanocomposite. Various combinations of the nanocomposite, the method of making the nanocomposite, and a method of disinfecting an aqueous solution with the nanocomposite, are also provided.

19 Claims, 13 Drawing Sheets

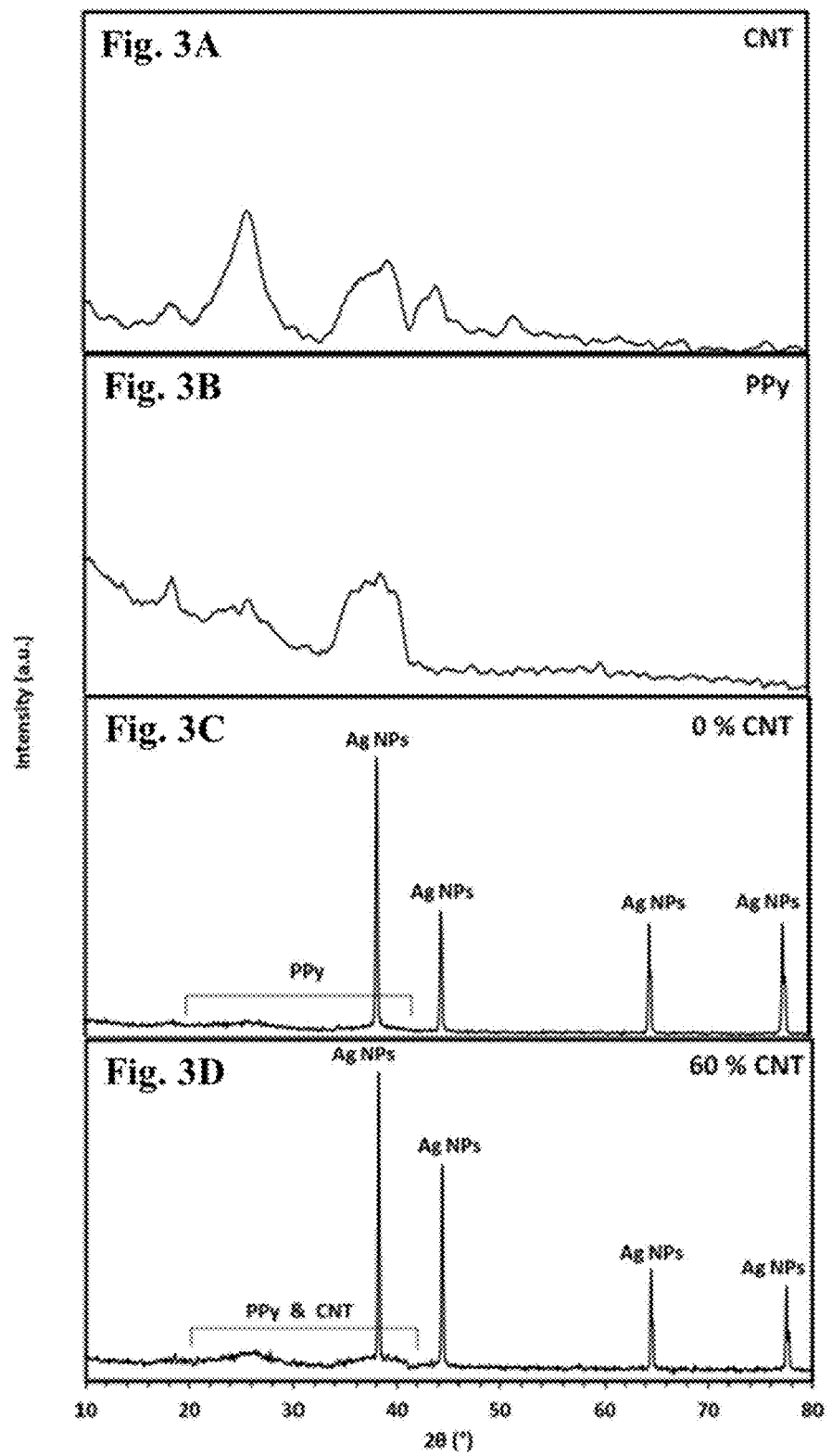

NANOCOMPOSITE AND A METHOD OF MAKING THE SAME

STATEMENT OF FUNDING ACKNOWLEDGEMENT

The authors acknowledge the support provided by the Deanship of Scientific Research (DSR), King Abdulaziz University, Jeddah, for funding through the grant no. 1433/130/359.

BACKGROUND OF THE INVENTION

Technical Field

The present invention relates to a nanocomposite that includes a core containing silver nanoparticles and a shell that includes polypyrrole and carbon nanotubes.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Pathogenic bacteria, as the main cause for life-threatening human diseases, have become more resistant against antibiotics. Research studies have been focused on finding effective alternatives for antibiotics [K. Vasilev, V. Sah, K. Anselme, C. Ndi, M. Mateescu, B. Dollmann, P. Martinek, H. Ys, L. Ploux and H. J. Griesser, Nano Lett., 2010, 10, 202-207; T. Iwase, Y. Uehara, H. Shinji, A. Tajima, H. Seo, K. Takada, T. Agata and Y. Mizunoe, Nature, 2010, 465, 346-349; K. Roy, G. M. Hilliard, D. J. Hamilton, J. Luo, M. M. Ostmann and J. M. Fleckenstein, Nature, 2009, 457, 594-598; T. Sibanda and A. I. Okoh, African Journal of Biotechnology, 2007, 6, 2886-2896; M. H. Kollef, Y. Golan, S. T. Micek, A. F. Shorr and M. I. Restrepo, Clin Infect Dis. 2011]. On the other hand, global demand for water free from pathogenic bacteria encourages researchers to design and/or develop new materials for effective and inexpensive water disinfection processes.

Recent studies revealed that nanomaterials are effective antimicrobial agents [Mahendra Rai (ed.), Nano-antimicrobials: progress and prospects (Springer, Berlin, Heidelberg, 2012); N. T. K. Thanh and L. A. W. Green, Nano Today, 2010, 5, 213-230; P. Singh, Y. J. Kim, H. Singh, C. Wang, K. H. Hwang, M. E. Farh, and D. C. Yang, Int. J. Nanomedicine, 2015, 10, 2567-2577; F. Heidarpour, W. A. Wan Ab Karim Ghani, A. Fakhru'l-Razi, S. Sobri, V. Heydarpour, M. Zargar and M. R. Mozafari, Clean Techn. Environ. Policy., 2011, 13, 499-507; A. Zane, R. F. Zuo, F. A. Villamena, A. Rockenbauer, F. A. M. Digeorge, K. Flores, P. K. Dutta and A. Nagy, Int. J. Nanomedicine, 2016, 11, 6459-6470; S. C. Smith and D. F. Rodrigues, Carbon, 2015, 91, 122-143]. Among nanomaterials, nanocomposites are one of the promising materials that provide a wide range of applications [R. M. El-Shishtawy, M. A. Salam, M. A. Gabal and A. M. Asiri, Polymer Composites, 2012, 33, 532-539; X. Yang, L. Li and F. Yan, Sensors and Actuators B: Chemical, 2010, 145, 495-500; M. A. Salam, M. S. I. Makki and M. Y. Abdelaal, Journal of Alloys and Compounds 2011, 509, 2582-2587]. Nanocomposites refer to composites of two or more components with at least one component being on a nanoscale. Nanocomposites can be engineered to form materials with improved mechanical properties [Z. Hu, G. Chen, Adv. Mater. 2014, 26, 5950-5956], improved thermoelectric performance [C. Gao, G. Chen, Composites Science and Technology 2016, 124, 52-70; K. Xu, G. Chen, D. Qiu, J. Mater. Chem. A, 2013, 1, 12395-12399; R. M. El-Shishtawy, M. Abdel Salam, M. A. Gabal, A. M. Asiri, Polymer Composites, 2012, 33, 532-539], improved thermal stability [J. Liu, G. Chen, J. Yang, Polymer 2008, 49, 3923-3927], etc.

Polypyrrole (PPy) is a conducting polymer that has been widely used in nanoscience and nanotechnology due to exceptional electrical properties, and controllable chemical and electrochemical properties, as well as the performance towards forming $\pi$-conjugated polymeric chains and reversible doping/de-doping processes [M. A. Salam, M. S. I. Makki and M. Y. Abdelaal, Journal of Alloys and Compounds 2011, 509, 2582-2587; C. Merlini, B. S. Rosa, D. Müller, L. G. Ecco, S. D. A. S Ramôa and G. M. O. Barra, Polymer Testing, 2012, 31, 971-977; M. A. Chougule, D. S. Dalavi, S. Mali, P. S. Patil, A. V. Moholkar, G. L. Agawane, J. H. Kim, S. Sen and V. B. Patil, Measurement, 2012, 45, 1989-1996]. The biocidal effect of PPy is likely attributed to the positive charges that can coordinate with the negatively charged bacteria and thereby causing death of the bacteria [F. A. G. da Silva Jr., J. C. Queiroz, E. R. Macedo, A. W. C. Fernandes, N. B. Freire, M. M. da Costa and H. P. de Oliveira, Materials Science and Engineering C, 2016, 62, 317-322; A. Varesano, C. Vineis, C. Tonetti, G. Mazzuchetti and V. Bobba, J. Appl. Polym. Sci., 2015, 132, 41670-41676; A. Varesano, A. Aluigi, L. Florio and R. Fabris, Synth. Met., 2009, 159, 1082-1089].

On the other hand, the high affinity of silver nanoparticles (AgNPs) towards sulfur-containing amino acids and the phosphor atoms presents in the DNA of bacteria causes death or inactivation of the bacteria [J. Upadhyay, A. Kumar, B. Gogoi and A. K. Buragohain, Mater. Sci. Eng. C, 2015, 54, 8-13; R. V. Ravishankar and B. A. Jamuna, Nanoparticles and their potential application as antimicrobials, in: A. Méndez-Vilas (Ed.), Science against Microbial Pathogens: Communicating Current Research and Technological Advances, Formatex, Badajoz 2011, pp. 197-209; M. Rai, A. Yadav and A. Gade, Biotechnol. Adv., 2009, 27, 76-83]. Recent studies indicated that AgNPs are not stable in aqueous solutions and form AgNPs aggregates. Aggregation of silver nanoparticles generally reduces their antibacterial activity [Prucek R I, Tuček J, Kilianová M, A. Panáček, L. Kvitek, J. Filip, M. Kolář K. Tománková and R. Zbořil, Biomaterials, 2011, 32, 4704-4713]. Also, silver nanoparticles are toxic to the human body. The cytotoxicity of AgNPs can be mainly attributed to the release of silver ions that induce the production of reactive oxygen species [Q. H. Tran, V. Q. Nguyen, and A.-T. Le, Advances in Natural Sciences: Nanoscience and Nanotechnology, 2013, 4, no. 3, Article ID033001]. Accordingly, biocidal efficacy of polypyrrole has been evaluated on silver-containing fabrics at different polypyrrole loadings [A. Varesano, C. Vineis, C. Tonetti, G. Mazzuchetti and V. Bobba, J. Appl. Polym. Sci., 2015, 132, 41670-41676].

Carbon nanotubes (CNTs) [S. Iijima, Nature, 1991, 354, 56-58] have also been comprehensively used in multidisciplinary research studies due to the unique physical and chemical properties. Accordingly, they have been widely used in a broad range of applications such as catalysts [X. Weilin, L. Changpeng, X. Wei and L. Tianhon, Electrochem. Commun., 2007, 9, 180-184], different biological aspects [A. Bianco and M. Prato, Adv. Mater., 2003, 15, 1765-1768; M. G. Zhang, A. Smith and W. Gorski, Anal. Chem., 2004, 76, 5045-5050; P. He and L. Dai, Chem. Commun., 2004, 3, 348-349; I. Heller, J. Kong, H. A. Heering, K. A. Williams, S. G. Lemay and C. Dekker, Nano Lett., 2005, 5, 137-142; M. J. Cloninger, Curr. Op. Chem. Biol., 2002, 6, 742-748; B. R. Azamian, J. J. Davis, K. S. Coleman, C. Bagshaw and M. L. H. Green, J. Am. Chem. Soc., 2002, 124, 12664-12665; C. McClory, T. McNally, G. P. Brennan, J. Erskine, J. Appl. Poly. Sci., 2007, 105, 1003-1011], nanoscale electronics [T. E. Karakasidis, C. A. Charitidis, Mater. Sci. Eng. C, 2007, 27, 1082-1089; A. B. Dalton, A. Ortiz-Acevedo, V. Zorbas, E. Brunner, W. M. Samson, S. Collins, J. M. Razal, M. Miki Yoshida, R. H. Baughman, R. K. Draper, I. H. Musselman, M. Jose-Yacaman and G. R. Dieckmann, Adv. Funct. Mater., 2004, 14, 1147-1151; C. K. M. Fung, V. T. S. Wong, R. H. M. Chan and W. J. Li, Nanotechnol, IEEE Transact, 2004, 3, 395-403], etc. When used as microorganism disinfectants, CNTs were shown to effectively kill bacteria by perturbing and/or disrupting the bacteria cell membranes [S. Baoukina, L. Monticelli and D. P. Tieleman, J. Phys. Chem. B, 2013, 117, 12113-12123]. CNTs/AgNPs composites have been demonstrated to effectively disinfect contaminated solutions [Y. N. Chang, J. L. Gong, G. M. Zeng, X. M. Ou, B. Song, M. Guo, J. Zhang and H. Y. Liu, Process Safety and Environmental Protection, 2 0 1 6, 102, 596-605; N. X. Dinh, D. T. Chi, N. T. Lan, H. Lan, H. V. Tuan, N. V. Quy, V. N. Phan, T. Q. Huy and A. T. Le, Appl. Phys. A, 2015, 119, 85-95; N. X. Dinh, N. V. Quy, T. Q. Huy and A. T. Le, Journal of Nanomaterials, Volume 2015, Article ID 814379].

In view of the forgoing, one objective of the present disclosure is to provide a nanocomposite that includes a core containing silver nanoparticles, and a shell that covers at least a portion of the core, wherein the shell includes polypyrrole and preferably carbon nanotubes. Accordingly, the silver nanoparticles are present in the nanocomposite in a weight range of 60 to 90 wt % and the polypyrrole is present in a weight range of 5 to 25 wt %, each being relative to the total weight of the nanocomposite. A weight ratio of the carbon nanotubes to the polypyrrole also lies within the range of 1:20 to 5:1. Another objective of the present disclosure is to provide a method of making the nanocomposite.

BRIEF SUMMARY OF THE INVENTION

According to a first aspect, the present disclosure relates to a nanocomposite including a core and a shell that covers at least a portion of the core, wherein the core includes silver nanoparticles and the shell includes polypyrrole, and wherein an amount of polypyrrole in the nanocomposite is in the range of 5 to 25 wt %, and an amount of silver nanoparticles in the nanocomposite is in the range of 60 to 90 wt %, each relative to the total weight of the nanocomposite.

In one embodiment, an average diameter of the silver nanoparticles is in the range of 1 to 100 nm.

In one embodiment, the shell covers at least 60% of an external surface area of the core.

In one embodiment, the shell has a thickness of no more than 1 μm.

In one embodiment, the shell further includes carbon nanotubes that are dispersed in the polypyrrole.

In one embodiment, a weight ratio of the carbon nanotubes to the polypyrrole is in the range of 1:20 to 5:1.

In one embodiment, the carbon nanotubes are single-walled carbon nanotubes with an average diameter in the range of 1 to 20 nm.

In one embodiment, the carbon nanotubes are multi-walled carbon nanotubes with an outer diameter in the range of 30 to 100 nm.

According to a second aspect, the present disclosure relates to a method of making a nanocomposite, involving i) mixing pyrrole with water and stirring to form a first mixture, ii) mixing a silver-containing solution with the first mixture and stirring for up to 30 hours to form a second mixture, wherein the pyrrole coordinates with silver ions present in the silver-containing solution, iii) storing the second mixture, thereby reducing the silver ions to silver nanoparticles while concurrently oxidizing the pyrrole to form polypyrrole via an oxidative polymerization, thereby forming the nanocomposite having a core comprising silver nanoparticles and a shell comprising polypyrrole.

In one embodiment, the first mixture is stirred at a temperature of 15 to 35° C.

In one embodiment, the second mixture is stored at a temperature of 15 to 35° C. for up to 10 days at an illuminance of no more than 50 lux.

In one embodiment, the silver-containing solution is an aqueous silver nitrate solution, and a molar ratio of the pyrrole to silver nitrate is in the range of 1:1 to 1:5.

In one embodiment, the method of making the nanocomposite further involves mixing a carbon nanotube suspension with the first mixture and sonicating prior to mixing the silver-containing solution with the first mixture, to form a nanocomposite having a core comprising silver nanoparticles and a shell comprising polypyrrole and carbon nanotubes.

According to a third aspect, the present disclosure relates to a method of disinfecting an aqueous solution including *Staphylococcus aureus* cells; the method involves contacting the aqueous solution with the nanocomposite to remove at least a portion of *Staphylococcus aureus* cells, wherein no more than 50 milliliters of the aqueous solution is contacted per one gram of the nanocomposite.

In one embodiment, a ratio of a number of viable *Staphylococcus aureus* cells per one milliliter of the aqueous solution after the contacting to the number of viable *Staphylococcus aureus* cells per one milliliter of the aqueous solution before the contacting is in the range of 1:5 to 1:10,000.

In one embodiment, the aqueous solution further includes *Escherichia coli* cells, wherein a ratio of a number of viable *Escherichia coli* cells per one milliliter of the aqueous solution after the contacting to the number of viable *Escherichia coli* cells per one milliliter of the aqueous solution before the contacting is in the range of 1:5 to 1:100.

In one embodiment, a weight ratio of the carbon nanotubes to the polypyrrole in the nanocomposite is in the range of 1:10 to 1:1, wherein a ratio of a number of viable *Escherichia coli* cells per one milliliter of the aqueous solution after the contacting to the number of viable *Escherichia coli* cells per one milliliter of the aqueous solution before the contacting is in the range of 1:100 to 1:10,000.

In one embodiment, the aqueous solution further includes one or more bacteria cells selected from the group consisting of *Klebsiella pneumonia, Chlamydia trachomatis, Neisseria gonorrhoeae, Yersinia pestis, Clostridium tetani, Providencia stuartii,* Pneumobacillus, *Vibrio vulnificus, Candida albicans, Bacillus cloacae, Pseudomonas maltophila, Pseudomonas aeruginosa, Streptococcus hemolyticus* B, *Citrobacter,* and *Salmonella paratyphi* C, wherein a ratio of a number of viable bacteria cells per one milliliter of the aqueous solution after the contacting to the number of viable bacteria cells per one milliliter of the aqueous solution before the contacting is in the range of 1:2 to 1:100.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3A represents an XRD spectrum of the CNTs.

FIG. 3B represents an XRD spectrum of the PPy.

FIG. 3C represents an XRD spectrum of the nanocomposite of PPy and AgNPs.

FIG. 3D represents an XRD spectrum of the nanocomposite of PPy, AgNPs, and 60 wt % CNTs, wherein the weight percent of CNT is relative to the weight of the PPy.

DETAILED DESCRIPTION OF THE EMBODIMENTS

Figure 1:
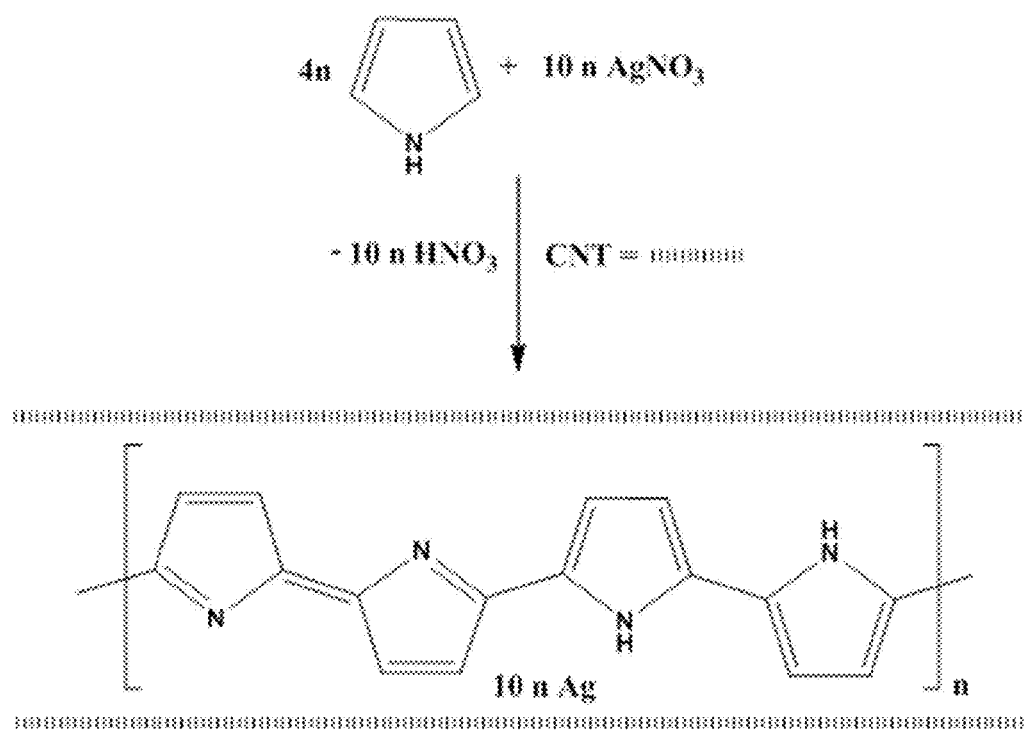
FIG. 1 represents a mechanism of forming a nanocomposite that includes silver nanoparticles (AgNPs), polypyrrole (PPy), and carbon nanotubes (CNTs).

Referring now to the drawings, wherein like reference numerals designate identical or corresponding parts throughout the several views.

According to a first aspect, the present disclosure relates to a nanocomposite (or nanocomposites). The term "nanocomposite" in this disclosure refers to a composition of at least two materials, wherein at least one of said materials has a size in a nanoscale range (i.e. in the range of less than 100 nm, preferably less than 80 nm).

The nanocomposite includes a core and a shell that covers at least a portion of the core. The core of the nanocomposite contains silver nanoparticles (AgNPs) in an elemental (or zero-valent) form, although cations of silver may also be present in the core. In addition, the shell of the nanocomposite contains one or more conducting polymers, preferably polypyrrole (PPy), and preferably may also include one or more carbon allotropes, preferably carbon nanotubes.

Figure 4A:
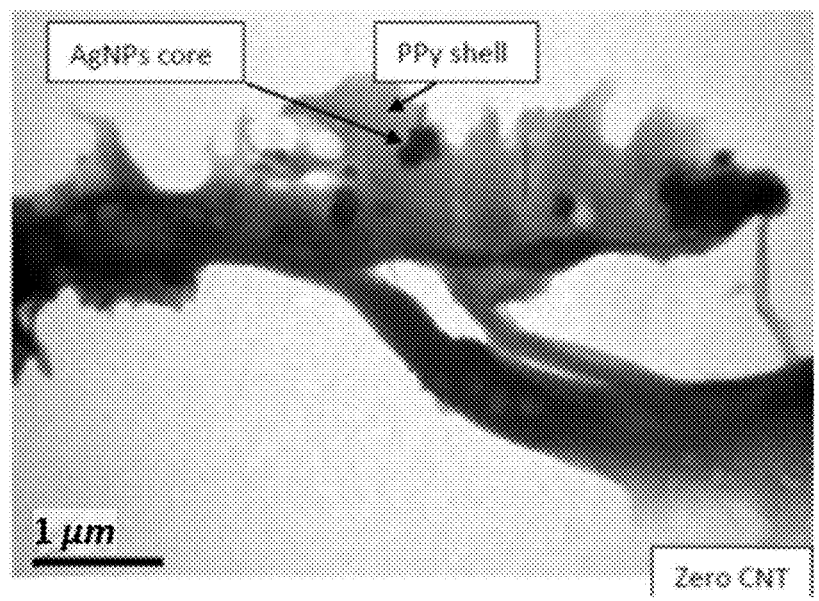
FIG. 4A is a TEM micrograph of the nanocomposite of PPy and AgNPs.

The nanocomposites may have an irregular morphology, due to an aggregation of silver nanoparticles that are covered by the shell, as shown in FIG. 4A. Accordingly, a size of the nanocomposite lies in a range from about 10 nm to about 10 µm, preferably from about 20 nm to about 1 µm, preferably from about 50 nm to about 500 nm, preferably from about 80 nm to about 200 nm. Also, a portion of the nanocomposites may also have a regular morphology, for example, including a nanosphere morphology, a nanosheet morphology, a nanotube morphology, a nanofiber morphology, a nanowire morphology, a nanohair morphology, a nanopillar morphology, a nanodisk morphology, a nanocube morphology, a nanorod morphology, a nanoring morphology, and/or a nanostar morphology. In view of this embodiment, the size of the nanocomposite may vary in the range from about 1 nm to about 1 mm, preferably from about 5 nm to about 100 µm, preferably from about 10 nm to about 50 µm, preferably from about 20 nm to about 20 µm, preferably from about 50 nm to about 10 µm, preferably from about 70 nm to about 5 µm, preferably from about 80 nm to about 1 µm, preferably from about 100 nm to about 500 nm, preferably from about 150 nm to about 400 nm, preferably from about 200 nm to about 300 nm.

The nanocomposite includes 60 to 90 wt %, preferably 65 to 88 wt %, preferably 70 to 85 wt %, preferably 75 to 82 wt %, preferably about 80 wt % of silver nanoparticles, relative to the total weight of the nanocomposite. Preferably, the silver nanoparticles are not aggregated, and an average diameter of the silver nanoparticles may preferably vary in the range of 1 to 100 nm, preferably 5 to 90 nm, preferably 10 to 80 nm, preferably 15 to 60 nm, preferably about 20 to 50 nm. In a preferred embodiment, the silver nanoparticles are substantially spherical with an average diameter of less than 50 nm, preferably less than 40 nm, preferably less than 30 nm, preferably less than 20 nm, preferably less than 10 nm, preferably less than 5 nm. In some embodiments, an average specific surface area of the silver nanoparticles present in the core of the nanocomposite vary in the range between 0.05 to 50 $m^2/g$, preferably 0.5 to 20 $m^2/g$, preferably 1 to 10 $m^2/g$, preferably 2 to 8 $m^2/g$, preferably 3 to 6 $m^2/g$, preferably about 5 $m^2/g$. Aggregation of the silver nanoparticles may adversely affect an anti-bacterial performance of the nanocomposite, due to a reduced surface area of the silver nanoparticles. In some embodiments, the silver nanoparticles are aggregated, and the size of aggregated silver nanoparticles vary in the range from about 100 nm to about 1 µm, preferably from about 150 nm to about 800 nm, preferably from about 180 nm to about 600 nm, preferably from about 200 nm to about 500 nm, preferably from about 250 nm to about 450 nm. Accordingly, an average specific surface area of the silver nanoparticles, in aggregated state, is in the range of 0.05 to 10 m$^2$/g, preferably 0.5 to 5 m$^2$/g, preferably 1 to 4 m$^2$/g, preferably 1.5 to 3 m$^2$/g.

In addition to the silver nanoparticles, the core of the nanocomposite may further include nanoparticles of one or more transition metals selected from gold (Au), platinum (Pt), palladium (Pd), copper (Cu), molybdenum (Mo), iron (Fe), iron oxide, tantalum (Ta), tin (Sn), titanium (Ti), and zinc (Zn).

In some embodiments, the shell covers at least 60%, preferably at least 65%, preferably at least 70%, preferably at least 75%, preferably at least 80%, but no more than 90%, preferably no more than 85% of an external surface area of the core. Accordingly, at least 10%, preferably about 10% to about 15% of the external surface area of the core is not covered by the shell, and therefore, the silver nanoparticles may be directly exposed to bacteria or other microorganisms present in a solution being contacted with the nanocomposite. In some other embodiments, the shell has a thickness of no more than 1 µm, preferably in the range of 5 to 500 nm, preferably 10 to 450 nm, preferably 20 to 400 nm, preferably 50 to 350 nm, preferably 80 to 300 nm, preferably 100 to 250 nm.

The nanocomposite includes 5 to 25 wt %, preferably 8 to 20 wt %, preferably 10 to 18 wt %, preferably 12 to 15 wt % of polypyrrole (PPy), with each weight percent being relative to the total weight of the nanocomposite. In some embodiments, the nanocomposite further includes one or more conducting polymers in the shell of the nanocomposite, including but not limited to, polyacetylene, polyphenylene vinylene, and polyphenylene sulfide, polythiophene, poly-PEDOT (poly(3,4-ethylenedioxythiophene)), polyaniline, polyindole, poly(3-methylthiophene), poly(N-methyl aniline), poly(o-toluidine), or derivatives and/or mixtures thereof. When present, the nanocomposite may include less than 10 wt %, preferably less than 8 wt %, preferably less than 5 wt % of the one or more conducting polymers.

Preferably, the polypyrrole, which is present in the shell of the nanocomposite, has an amorphous structure. Said polypyrrole is preferably a linear chain polymer with a weight-average molecular weight in the range of 1,000 to 1,000,000 Da (Dalton), preferably 10,000 to 500,000 Da, preferably 20,000 to 400,000 Da, preferably 30,000 to 300,000 Da, preferably 50,000 to 200,000 Da. In some embodiments, a portion of the polypyrrole may be present in a non-linear polymer form, e.g. in a form of a brushed polymer, or a branched polymer, or a crosslinked polymer. Preferably, said non-linear portion of the polypyrrole is no more than 10 wt %, preferably no more than 5 wt %, preferably no more than 2 wt %, relative to the total weight of the polypyrrole.

In some embodiments, one or more substituted pyrroles are used to form a substituted polypyrrole. Preferably, the substituted pyrrole may be 3-substituted pyrrole to form 3-substituted polypyrrole. Alternatively, the pyrrole may have at least one substituted group selected from a hydroxyl, a halogen atom, a cyano, a nitro, an alkyl, a cycloalkyl, a cycloalkylalkyl, an arylalkyl, a heteroaryl, and an aryl. The term "alkyl" as used herein refers to a straight or branched hydrocarbon fragment, with a general formula of $C_nH_{2n+1}$, wherein n ranges from 1 to 20, preferably 1 to 10. Exemplary alkyls include, but are not limited to, methyl, ethyl, propyl, isopropyl, butyl, isobutyl, t-butyl, pentyl, isopentyl, neopentyl, and hexyl. The term "cycloalkyl" as used refers to a cyclic alkyl having 3 to 12, preferably 4 to 7 carbon atoms including, but not limited to, cyclopropyl, cyclobutyl, cyclopentyl, cyclohexyl, cycloheptyl. The term "cycloalkylalkyl" as used herein refers to an alkyl moiety that is substituted by one or more cycloalkyl groups. The term "arylalkyl" as used herein refers to an aryl group that is attached to an alkyl group (e.g., benzyl, phenethyl, pyridylmethyl, etc.). The term "heteroaryl" as used in this disclosure refers to 5 to 10 membered mono- or fused-heteroaromatic rings which have at least one hetero atom selected from nitrogen, oxygen, and sulfur, and includes, for example, 2-furyl, 3-furyl, 2-thienyl, 3-thienyl, 2-pyridyl, 3-pyridyl, 4-pyridyl, pyrazolyl; imidazolyl, pyrimidinyl, pyridazinyl, pyrazinyl, benzimidazolyl, quinolyl, oxazolyl, thiazolyl, indolyl. The term "aryl" as used herein refers to phenyl, biphenyl, naphthyl, anthracenyl, and may also refer to heteroaryl including furyl, imidazolyl, triazolyl, triazinyl, oxazolyl, isoxazolyl, thiazolyl, isothiazolyl, pyrazolyl, pyrrolyl, pyrazinyl, tetrazolyl, and pyridyl.

Figure 4B:
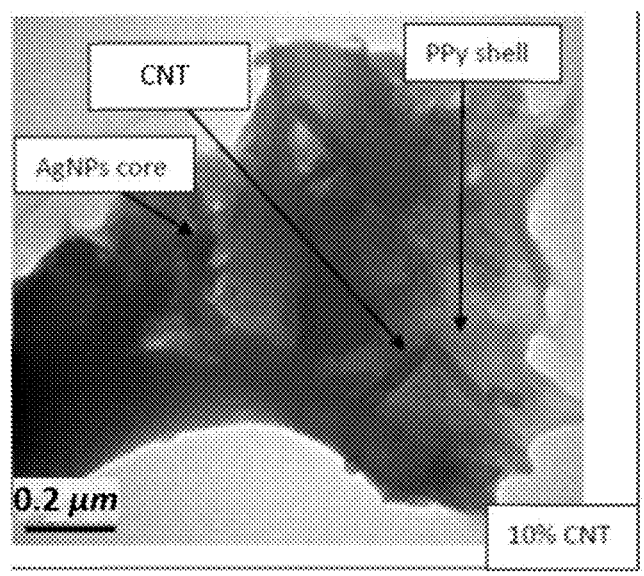
FIG. 4B is a TEM micrograph of the nanocomposite of PPy and AgNPs, and 10 wt % CNTs, wherein the weight percent of CNT is relative to the weight of the PPy.
Figure 4C:
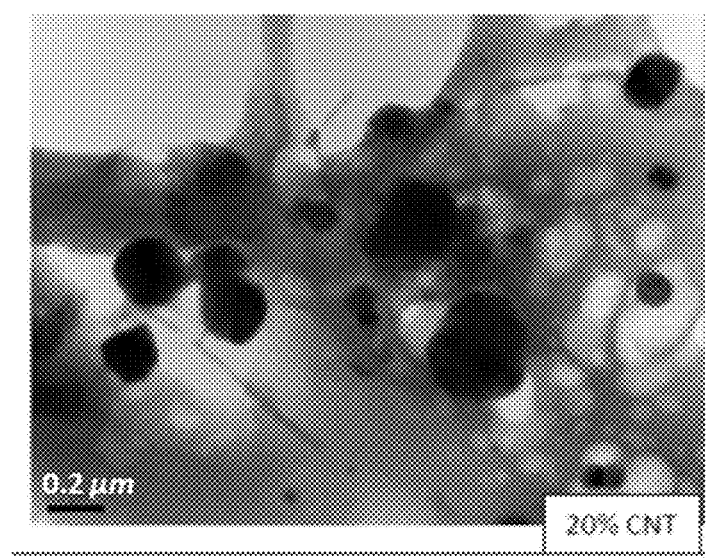
FIG. 4C is a TEM micrograph of the nanocomposite of PPy and AgNPs, and 20 wt % CNTs, wherein the weight percent of CNT is relative to the weight of the PPy.
Figure 4D:
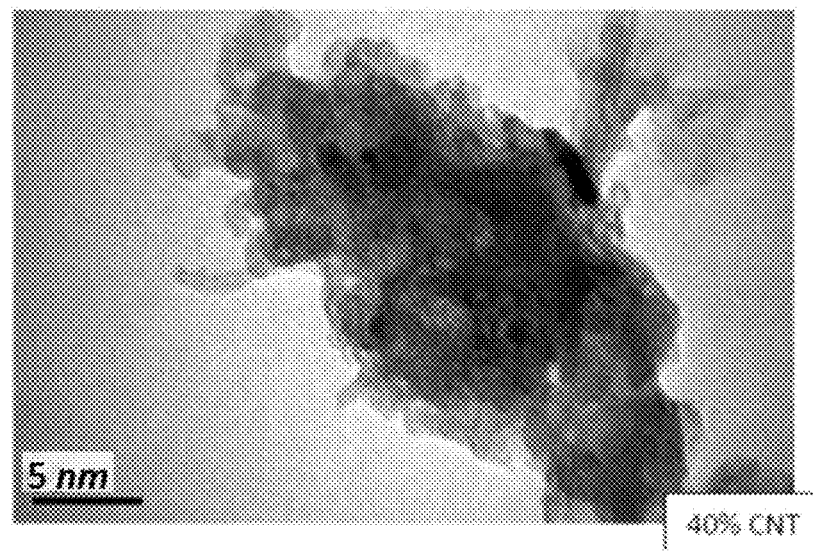
FIG. 4D is a TEM micrograph of the nanocomposite of PPy and AgNPs, and 40 wt % CNTs, wherein the weight percent of CNT is relative to the weight of the PPy.

In a preferred embodiment, the shell of the nanocomposite further includes carbon nanotubes that are dispersed in the polypyrrole. The shell may be a polymer composite with the polypyrrole (or the polypyrrole and the one or more conducting polymers) being a polymer phase and the carbon nanotubes being a filler phase. Said polymer composite may cover at least a portion of the external surface area of the core, which contains non-aggregated or aggregated silver nanoparticles. In another embodiment, the nanocomposite further includes carbon nanotubes, and the polypyrrole encapsulates (or covers) both the silver nanoparticles and the carbon nanotubes (i.e. the polypyrrole is a matrix for both the silver nanoparticles and the carbon nanotubes), as shown in FIG. 4B. In some embodiments, the carbon nanotubes (i.e. the filler phase) are dispersed in the polypyrrole (or the polypyrrole and the one or more conducting polymers), i.e. the polymer phase, wherein the at least at least 50%, preferably at least 60%, preferably at least 70%, preferably at least 80%, but no more than 90%, preferably no more than 85% of an external surface area of the carbon nanotubes are covered with the polymer phase, i.e. the polypyrrole (or the polypyrrole and the one or more conducting polymers).

In the embodiments where nanoparticles of the one or more transition metals are also present in the nanocomposite, said nanoparticles may preferably be present in the core and may preferably be partially covered with the shell.

A weight ratio of the carbon nanotubes to the polypyrrole may vary in the range between 1:20 to 5:1, preferably 1:18 to 4:1, preferably 1:15 to 3:1, preferably 1:12 to 2:1, preferably 1:10 to 1:1, preferably 1:8 to 1:1.2, preferably 1:5 to 1:1.5, preferably about 1:1.6. In a preferred embodiment, the carbon nanotubes are single-walled carbon nanotubes (SWCNTs) with an average diameter in the range of 1 to 20 nm, preferably 1.5 to 10 nm, preferably 2 to 5 nm, preferably no more than 3 nm. An aspect ratio, i.e. length-to-diameter, of the SWCNTs may be at least 50, preferably at least 100, preferably greater at least 1,000, preferably at least 10,000, preferably at least 100,000, but no more than 500,000. The single-walled carbon nanotubes may be closed structures having hemispherical caps at each end of respective tubes, or they may have a single open end or both open ends. The single-walled carbon nanotubes also may include a central hollow portion, which may be filled with the silver nanoparticles, the conducting polymers of the shell, preferably PPy, or other amorphous carbonaceous compounds.

In one embodiment, the carbon nanotubes are multi-walled carbon nanotubes (MWCNTs) with an outer diameter in the range of 30 to 100 nm, preferably 35 to 90 nm, preferably 40 to 80 nm, preferably 45 to 70 nm, preferably 50 to 60 nm. An aspect ratio, i.e. length-to-diameter, of the MWCNTs may be at least 50, preferably at least 100, preferably greater at least 1,000, but no more than 10,000, preferably no more than 5,000. The multi-walled carbon nanotubes may be closed structures having hemispherical caps at each end of respective tubes, or they may have a single open end or both open ends. The multi-walled carbon nanotubes also may include a central hollow portion, which may be filled with the silver nanoparticles, the conducting polymers of the shell, preferably PPy, or other amorphous carbonaceous compounds.

In another embodiment, the shell of the nanocomposite further includes various carbon allotropes including, for example, graphene and/or fullerene nanoparticles with an average particle size in the range of 0.5 to 500 nm, preferably 1 to 100 nm, preferably 2 to 50 nm, preferably 5 to 20 nm.

The presence of the silver nanoparticles, the carbon nanotubes, the polypyrrole, and optionally the one or more conducting polymers may provide a synergistic anti-bacterial property to the nanocomposite. An anti-bacterial property of PPy may be attributed to the presence of positive charges on oxidized PPy chains that may strongly interact with negatively charged bacteria, and thus hinder a movement of the bacteria. An anti-bacterial property of the silver nanoparticles may be associated with a strong affinity of the silver nanoparticles towards sulfur-containing amino acids present in bacteria cell membranes, as well as an affinity towards phosphor atoms present in a DNA of the bacteria. Furthermore, due to a very large specific surface area, carbon nanotubes may provide good bacterial inactivation efficiency by perturbing and/or disrupting microbial processes. In view of that, the nanocomposite may provide antimicrobial/antibacterial properties against a broad range of microorganisms such as bacteria, viruses, fungi, protozoa, etc. Exemplary bacteria include the *Escherichia* group such as *Escherichia coli* (*E. Coli*), the *Staphylococcus* group such as *Staphylococcus aureus*, the *Pseudomonas* group such as *Pseudomonas aeruginosa* or *Pseudomonas maltophila*, the *Acinetobacter* groups such as *Acinetobacter calcoaceticus*, the *Serratia* group, the *Klebsiella* group such as *Klebsiella pneumonia*, the *Enterobacter* group, the *Citrobacter* group, the *Burkholderia* group, the *Sphingomonas* group, the *Chromobacterium* group, the *Salmonella* group such as *Salmonella paratyphi* C, the *Vibrio* group such as *Vibrio vulnificus*, the *Legionella* group, the *Campylobacter* group, the *Yersinia* group, the *Proteus* group, the *Neisseria* group, the *Streptococcus* group such as *Streptococcus hemolyticus* B, the *Enterococcus* group, the *Clostridium* group, the *Corynebacterium* group, the *Listeria* group, the *Bacillus* group such as Pneumobacillus, the *Mycobacterium* group, the *Chlamydia* group such as *Chlamydia trachomatis*, the *Providencia* group such as *Providencia stuartii*, the *Providencia* group such as *Providencia stuartii*, the *Rickettsia* group, and the *Haemophilus* group. Furthermore, examples of a virus may be a hepatitis A virus, an adenovirus, a *rotavirus*, and a *norovirus*. Also, examples of fungi may include the *candida* group fungi such as *Candida albicans*. Examples of protozoa may include the *Cryptosporidium* group of protozoa.

In a preferred embodiment, one gram of the nanocomposite may adsorb at least $10^3$ CFU/mL (colony-forming units per milliliter), preferably at least $10^4$ CFU/mL, preferably $10^4$ to $10^5$ CFU/mL, preferably $5\times10^4$ to $10^5$ CFU/mL of one or more of the microorganisms. In another preferred embodiment, one gram of the nanocomposite may adsorb at least $10^3$ CFU/mL (colony-forming units per milliliter), preferably at least $10^4$ CFU/mL, preferably $10^4$ to $10^5$ CFU/mL, preferably $5\times10^4$ to $10^5$ CFU/mL of *Escherichia coli* (*E. coli*) in a liquid.

According to a second aspect, the present disclosure relates to a method of making the nanocomposite. Accordingly, a pyrrole is first mixed with water, preferably distilled water, and stirred to form a first mixture. Preferably, a mass concentration of the pyrrole in the first mixture is in the range of 0.5 to 1.5 g/100 ml (gram per 100 milliliter of water), preferably 0.5 to 1.5 g/100 ml, preferably 0.6 to 1.2 g/100 ml, preferably 0.7 to 1.0 g/100 ml, preferably about 0.75. The pyrrole may preferably be mixed with water at room temperature (i.e. a temperature in the range of 15 to 35° C., preferably 20 to 30° C., preferably 22 to 28° C., preferably about 25° C.). The pyrrole may be mixed with water in a dropwise manner with a mixing rate of no more than 0.5 L/min, preferably no more than 1.0 L/min. Alternatively, the pyrrole may be mixed with water at a mixing rate of at least 10 mL/s, preferably at least 20 mL/s, preferably at least 50 mL/s, preferably at least 100 mL/s, preferably at least 500 mL/s, but no more than 1.0 L/s. Preferably, the first mixture is stirred at a temperature in the range of 15 to 35° C., preferably 20 to 30° C., preferably 22 to 28° C., preferably about 25° C., for at least 1 hour, preferably at least 2 hours, preferably at least 4 hours, preferably at least 6 hours, but no more than 8 hours.

In addition to the pyrrole, one or more organic compounds may also be mixed with water to form the first mixture. Exemplary organic compounds include, but are not limited to phenylene vinylene, phenylene sulfide, thiophene, ethylenedioxythiophene, aniline, methyl aniline, indole, N-methyl thiophene, toluidine, or derivatives thereof.

In a preferred embodiment, a predetermined amount of carbon nanotubes may be mixed with the first mixture and stirred. Preferably, a ratio of the predetermined amount of carbon nanotubes to an amount of pyrrole in the first solution is in the range of 1:20 to 5:1, preferably 1:18 to 4:1, preferably 1:15 to 3:1, preferably 1:12 to 2:1, preferably 1:10 to 1:1, preferably 1:8 to 1:1.2, preferably 1:5 to 1:1.5, preferably about 1:1.6. The carbon nanotubes may be mixed with the first mixture in a dropwise manner with a mixing rate of no more than 0.5 L/min, preferably no more than 1.0 L/min. Alternatively, the carbon nanotubes may be mixed with the first mixture at a mixing rate of at least 10 mL/s, preferably at least 20 mL/s, preferably at least 50 mL/s, preferably at least 100 mL/s, but no more than 1.0 L/s. The first mixture may be stirred at a temperature in the range of 15 to 35° C., preferably 20 to 30° C., preferably 22 to 28° C., preferably about 25° C., for at least 1 hour, preferably at least 2 hours, preferably at least 4 hours, preferably at least 6 hours, but no more than 12 hours, preferably no more than 10 hours, after mixing the carbon nanotubes. The carbon nanotubes may be stirred with a mechanical stirrer or a magnetic stirrer with a rotational speed of 100 to 1,000 rpm, preferably 200 to 800 rpm, preferably 300 to 700 rpm.

In a preferred embodiment, the carbon nanotubes (CNTs) are first mixed with water to form a carbon nanotube suspension (a CNT suspension) prior to mixing the carbon nanotubes with the first mixture. The CNT suspension may preferably be sonicated or ultra-sonicated for at least 30 minutes, preferably at least 1 hour, preferably at least 2 hours, but no more than 6 hours, preferably no more than 5 hours. In addition, the CNT suspension may be roll-milled before and/or after sonicating the CNT solution. Preferably, the CNT solution may be rolled milled for at least 3 times, preferably at least 5 times, preferably at least 10 times, but no more than 20 times. Said sonicating and roll-milling steps may provide a CNT suspension with a good dispersion of CNT. In another preferred embodiment, a surfactant and/or an additive may also be mixed with water to prevent aggregation of carbon nanotubes in water and to provide a homogenous CNT suspension. Exemplary surfactants may include one or more of sodium dodecylbenzene sulfonate, sodium dodecyl sulfonate, toluene sulfonic acid, polystyrene sulfuric acid, etc.

In addition to the carbon nanotubes, one or more carbon allotropes may also be mixed with the first mixture. Exemplary carbon allotropes include, but are not limited to graphene and fullerene nanoparticles with an average particle size in the range of 0.5 to 500 nm, preferably 1 to 100 nm, preferably 2 to 50 nm, preferably 5 to 20 nm.

In another embodiment, the carbon nanotubes and/or the one or more carbon allotropes are acid-treated before mixing with the first mixture. Accordingly, the carbon nanotubes and/or the one or more carbon allotropes may be refluxed with an acid solution, e.g. an aqueous hydrochloric acid solution, an aqueous nitric acid solution, and/or an aqueous sulfuric acid solution, having a pH in the range of 1 to 5, preferably about 2 to 4 to convert at least a portion of hydroxyl groups that may be present on the surface of the carbon nanotubes and/or the one or more carbon allotropes to carboxylate functionalities.

The method of making the nanocomposite further involves mixing a silver-containing solution with the first mixture and stirring for up to 30 hours, preferably up to 24 hours, preferably up to 20 hours, preferably up to 15 hours, preferably up to 12 hours, preferably up to 10 hours, but no less than 8 hours, thereby forming a second mixture. The silver-containing solution may be mixed with the first mixture in a dropwise manner with a mixing rate of no more than 0.5 L/min, preferably no more than 1.0 L/min. Alternatively, the silver-containing solution may be mixed with the first mixture at a mixing rate of at least 10 mL/s, preferably at least 20 mL/s, preferably at least 50 mL/s, preferably at least 100 mL/s, but no more than 1.0 L/s. In a preferred embodiment, the silver-containing solution is stirred at a temperature in the range of 15 to 35° C., preferably 20 to 30° C., preferably 22 to 28° C., preferably about 25° C. The silver-containing solution may preferably be sonicated or ultra-sonicated for at least 30 minutes, preferably at least 1 hour, preferably at least 2 hours, but no more than 6 hours, preferably no more than 4 hours, prior to mixing with the first mixture. In the embodiments where carbon nanotubes or the CNT suspension is mixed with the first mixture, the silver-containing solution is mixed with the first mixture after mixing the carbon nanotubes or the CNT suspension.

In some embodiments, the silver-containing solution is at least one solution selected from an aqueous silver sulfate solution, an aqueous silver acetate solution, an aqueous silver nitrate solution, an aqueous silver cyclohexanebutyrate solution, an aqueous silver heptafluorobutyrate solution, an aqueous silver lactate solution, an aqueous silver pentafluoropropionate solution, an aqueous silver tetrafluoroborate solution, and an aqueous silver p-toluenesulfonate solution. However, in a preferred embodiment, the silver-containing solution is an aqueous silver nitrate solution, and a molar ratio of the pyrrole to silver nitrate in the second solution is in the range of 1:1 to 1:5, preferably 1:1.2 to 1:4.5, preferably 1:1.5 to 1:4, preferably 1:2 to 1:3.5, preferably 1:2.2 to 1:3, preferably about 1:2.5. In addition to the silver-containing solution, aqueous solutions of one or more transition metal salts may be mixed with the second mixture. Said transition metal salts include one or more transition metals selected from gold (Au), platinum (Pt), palladium (Pd), copper (Cu), molybdenum (Mo), iron (Fe), iron oxide, tantalum (Ta), tin (Sn), titanium (Ti), and zinc (Zn).

In one embodiment, a polymerization initiator may also be mixed with the first mixture after mixing the silver-containing solution and before stirring. The polymerization initiator may preferably be an oxidant such as ammonium persulfate. Preferably, the polymerization initiator may first be dissolved in water, if solid, and then mixed with the first mixture in a dropwise manner, i.e. with a mixing rate of no more than 0.2 L/min, preferably no more than 0.1 L/min.

The method of making the nanocomposite further involves storing the second mixture for up to 10 days, preferably up to 8 days, preferably up to 7 days, at a temperature in the range of 15 to 35° C., preferably 20 to 30° C., preferably 22 to 28° C., preferably about 25° C. In a preferred embodiment, the second mixture is stored in a dark place having an illuminance of no more than 50 lux, preferably no more than 5 lux, preferably in the range from about 0.0001 to about 1.0 lux, preferably from about 0.0005 to about 0.05 lux.

Figure 4E:
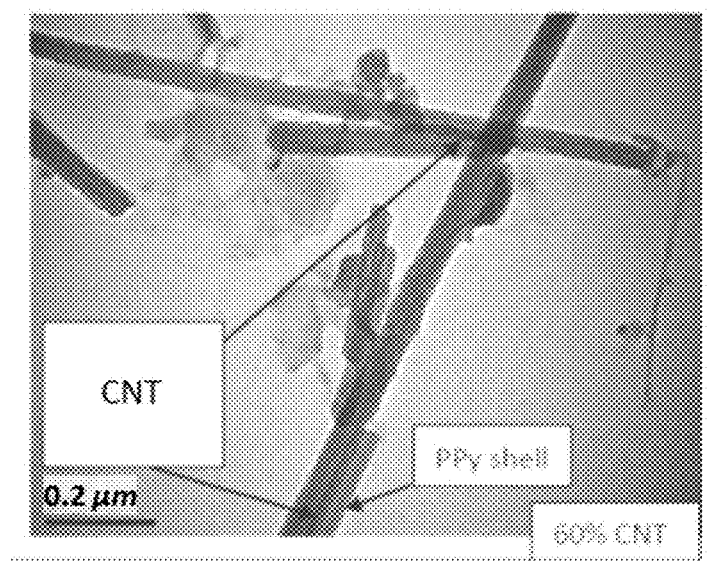
FIG. 4E is a TEM micrograph of the nanocomposite of PPy and AgNPs, and 60 wt % CNTs, wherein the weight percent of CNT is relative to the weight of the PPy.
Figure 4F:
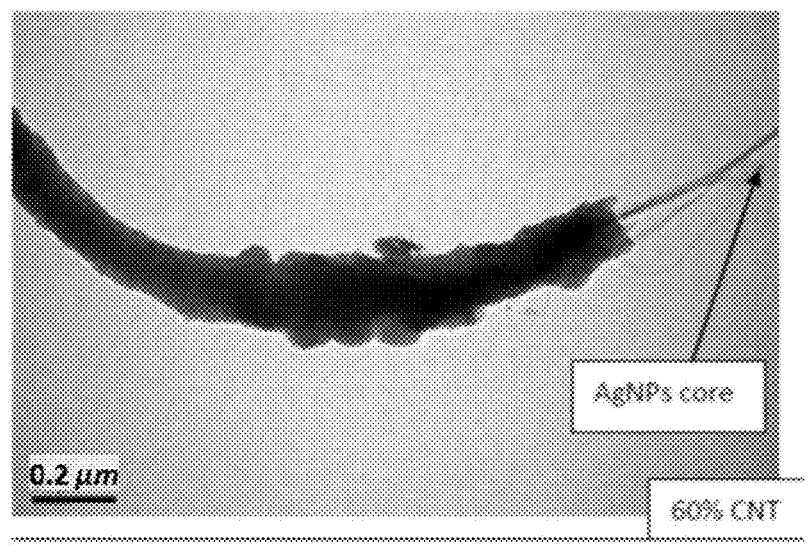
FIG. 4F is a TEM micrograph of the nanocomposite of PPy and AgNPs, and 60 wt % CNTs, wherein the weight percent of CNT is relative to the weight of the PPy.

In the embodiments where carbon nanotubes are present in the second mixture, the pyrrole may be adsorbed on at least a portion of a surface of the carbon nanotubes due to pi-pi and/or Van der Walls interactions. Accordingly, after mixing the silver-containing solution, the pyrrole coordinates with (or is adsorbed by) the silver cations present in the silver-containing solution due to the presence of a binding affinity between a nitrogen atom in the pyrrole and the silver cations. The pyrrole may oxidatively polymerize after mixing the silver-containing solution to the first mixture, or after stirring the second mixture, or after stirring and during storing the second mixture. In view of that, silver cations are reduced to silver atoms while concurrently oxidizing the pyrrole to polypyrrole, thereby forming the nanocomposite with a core including silver atoms, or silver cations, and a shell comprising polypyrrole that encapsulates the core. Representative TEM micrographs of the nanocomposite are shown in FIGS. 4A, 4B, 4C, 4D, 4E, and 4F. In the embodiments where carbon nanotubes are present in the second mixture, the shell is a polymer composite with the polypyrrole being the polymer phase and the carbon nanotubes being the filler phase, wherein the polymer composite encapsulates the core. In some embodiments, the nanocomposites that include carbon nanotubes may have nano-cylindrical (or nanowire) morphologies, since the polypyrrole encapsulates the carbon nanotubes, as shown in FIGS. 4E and 4F.

In some embodiments, the nanocomposite may be removed from the second mixture by centrifuging or filtering the second mixture. The nanocomposite may be washed with water, preferably deionized water, for at least three times, preferably 4 to 6 times. The nanocomposite may further be washed with an organic solvent, e.g. acetone, methanol, isopropyl alcohol, toluene, etc. for no more than 5 times, preferably no more than 3 times. The nanocomposite may be dried in a temperature range of 20 to 80° C., preferably 30 to 70° C., preferably 40 to 60° C., preferably about 50° C., and preferably in a sub-atmospheric pressure in the range of 0.1 to 0.95 atm, preferably 0.2 to 0.8 atm, preferably 0.3 to 0.7 atm, preferably 0.4 to 0.6 atm, for at least 6 hours, preferably 8 to 12 hours.

In one embodiment, a yield of forming the nanocomposite with the method that is described in the second aspect, is in the range of 50% to 85% w/w, preferably 55% to 80% w/w, preferably 60% to 75% w/w, preferably 65% to 70% w/w. The term "yield of forming the nanocomposite" as used in this disclosure refers to a ratio of a weight of the nanocomposite formed to a total weight of the pyrrole (or the organic compounds), the silver-containing solution, and the carbon nanotubes (or the one or more carbon allotropes).

According to a third aspect, the present disclosure relates to a method of disinfecting an aqueous solution by contacting the aqueous solution with the nanocomposite to remove at least a portion of microorganisms present in the aqueous solution.

The aqueous solution may be municipal drinking water, seawater, wastewater, or industrial wastewater before dumping, a water sample from a river, a lake, a pond, etc. Alternatively, the aqueous solution may be blood or a blood serum.

The microorganisms present in the aqueous solution may be one or more of bacteria, viruses, fungi, and protozoa, as described previously. A total concentration of the microorganisms in the aqueous solution may preferably be no more than $10^{10}$ CFU/mL, preferably no more than $10^9$ CFU/mL, preferably no more than $10^8$ CFU/mL, preferably no more than $10^6$ CFU/mL.

A disinfection efficiency of the nanocomposite with respect to the microorganisms may preferably be in the range of 1:2 to 1:10,000, preferably 1:5 to 1:5,000, preferably 1:8 to 1:1,000, preferably 1:10 to 1:500, preferably 1:20 to 1:400, preferably 1:50 to 1:200. The term "disinfection efficiency" as used herein refers to a ratio of a total number of the microorganisms present in one milliliter of the aqueous solution after contacting with one gram of the nanocomposite to the total number of the microorganisms present in one milliliter of the aqueous solution before contacting with one gram of the nanocomposite.

In a preferred embodiment, a volume of the aqueous solution which is contacted with one gram of the nanocomposite is no more than 50 milliliter (mL), preferably no more than 30 mL, preferably no more than 10 mL, preferably in the range from about 2 to about 8 mL, preferably about 5 mL.

In some embodiments, the aqueous solution includes *Staphylococcus aureus* before contacting with the nanocomposite, and the disinfection efficiency of the nanocomposite with respect to the *Staphylococcus aureus* is in the range of 1:5 to 1:10,000, preferably 1:10 to 1:1,000, preferably 1:20 to 1:500, preferably 1:30 to 1:400, preferably 1:50 to 1:300, preferably about 1:200. In a preferred embodiment, the nanocomposite does not include carbon nanotubes, and preferably does not include the carbon allotropes, wherein the disinfection efficiency of the nanocomposite with respect to the *Staphylococcus aureus* is in the range of 1:100 to 1:1,000, preferably 1:120 to 1:500, preferably 1:150 to 1:400.

In some embodiments, the aqueous solution includes *Escherichia coli* (*E. coli*) before contacting with the nanocomposite and the disinfection efficiency of the nanocomposite with respect to the *E. coli* is in the range of 1:5 to 1:10,000, 1:10 to 1:5,000, preferably 1:20 to 1:1,000, preferably 1:50 to 1:800, preferably 1:100 to 1:500. In one embodiment, the nanocomposite does not include carbon nanotubes, and also does not include the carbon allotropes, wherein the disinfection efficiency of the nanocomposite with respect to the *E. coli* is in the range of 1:5 to 1:100, preferably 1:8 to 1:100, preferably 1:10 to 1:100. In a preferred embodiment, the nanocomposite includes carbon nanotubes, and may also include the carbon allotropes, wherein the disinfection efficiency of the nanocomposite with respect to the *E. coli* is in the range of 1:5 to 1:10,000, preferably 1:10 to 1:5,000, preferably 1:100 to 1:1,000, preferably 1:120 to 1:500, preferably 1:150 to 1:400. In another preferred embodiment, the nanocomposite includes carbon nanotubes and a weight ratio of the carbon nanotubes to the polypyrrole in the nanocomposite is in the range of 1:10 to 1:1, preferably 1:8 to 1:1.2, preferably 1:5 to 1:1.4, preferably 1:2 to 1:1.5, preferably about 1:1.6, wherein the disinfection efficiency of the nanocomposite with respect to the *E. coli* is in the range of 1:100 to 1:10,000, preferably 1:200 to 1:5,000, preferably 1:500 to 1:1,000.

In some embodiments, the aqueous solution includes one or more bacteria selected from the group consisting of *Klebsiella pneumonia, Chlamydia trachomatis, Neisseria gonorrhoeae, Yersinia pestis, Clostridium tetani, Providencia stuartii,* Pneumobacillus, *Vibrio vulnificus, Candida albicans, Bacillus cloacae, Pseudomonas maltophila, Pseudomonas aeruginosa, Streptococcus hemolyticus* B, *Citrobacter,* and *Salmonella paratyphi* C, before contacting with the nanocomposite. Accordingly, the disinfection efficiency of the nanocomposite with respect to the one or more bacteria is in the range of 1:2 to 1:100, preferably 1:5 to 1:100, preferably 1:10 to 1:100, preferably 1:20 to 1:100.

The aqueous solution may be contacted with the nanocomposite in a continuous mode or in a batch mode. In one embodiment, the aqueous solution with a volumetric flow rate in the range of 0.1 to 100 mL/min, preferably 0.2 to 50 mL/min, preferably 0.3 to 10 ml/min, preferably 0.4 to 5 mL/min, preferably 0.5 to 1.0 mL/min is passed through the nanocomposite. In an alternative embodiment, the aqueous solution with a volumetric flow rate in the range of 1.0 to 1,000 L/min, preferably 5 to 800 L/min, preferably 10 to 500 L/min, preferably 50 to 400 L/min, preferably 100 to 300 L/min is passed through the nanocomposite. Yet in another embodiment, the aqueous solution is contacted with the nanocomposite in a batch mode, wherein a predetermined volume of the aqueous solution is contacted with the nanocomposite for a predetermined amount of time. The predetermined volume may be no more than 50 mL, preferably no more than 30 mL, preferably no more than 10 mL, preferably in the range from about 2 to about 8 mL, preferably about 5 mL, per one gram of the nanocomposite. The predetermined amount of time may vary in the range between 10 seconds to 48 hours, preferably 30 seconds to 5 hours, preferably 1 minute to 1 hour, preferably about 2 minutes.

In some embodiments, the aqueous solution may be sonicated during contacting with the nanocomposite. Accordingly, the aqueous solution may be sonicated for at least 1 minute, preferably at least 5 minutes, preferably at least 30 minutes, but no more than 1 hour, during the contacting.

Figure 6:
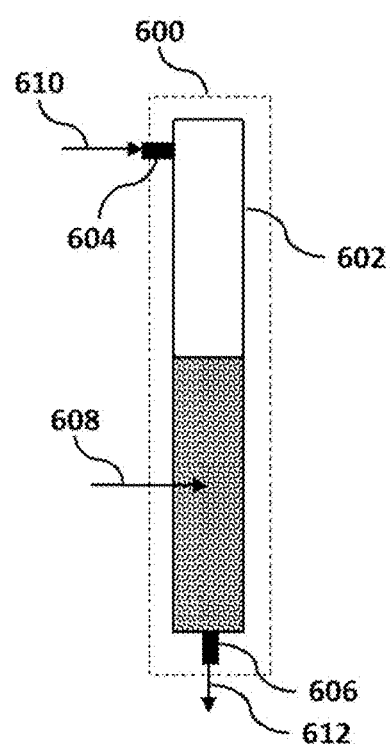
FIG. 6 is a schematic diagram of a water disinfecting column.

Referring to FIG. 6; another aspect of the present disclosure relates to a water disinfecting column 600. The water disinfecting column 600 includes a vessel 602 with an internal cavity, an inlet 604 configured to deliver contaminated water 610 to the internal cavity, an outlet 606 configured to reject disinfected water 612 from the internal cavity. The water disinfecting column 600 further includes the nanocomposites 608, preferably in the form of particles with an average particle size in the range of 1 nm to about 1 mm, preferably from about 5 nm to about 100 μm, preferably from about 10 nm to about 50 μm, preferably from about 20 nm to about 20 μm, preferably from about 50 nm to about 10 μm, preferably from about 70 nm to about 5 μm, preferably from about 80 nm to about 1 μm, preferably from about 100 nm to about 500 nm, preferably from about 150 nm to about 400 nm, preferably from about 200 nm to about 300 nm, that are disposed in the internal cavity of the vessel 602. The vessel may have a volume in the range of 0.01 to 10,000 L, preferably 0.1 to 5,000 L, preferably 0.5 to 3,000 L, preferably 1.0 to 2,000 L, preferably 10 to 1,000 L, preferably 50 to 500 L. The nanocomposites 608 are preferably packed in the vessel 602, wherein the nanocomposites 608 occupy at least 20%, preferably at least 30%, preferably at least 40%, preferably at least 50%, preferably at least 60%, preferably at least 70%, preferably at least 80%, but no more than 90% of the total volume of the vessel. In one embodiment, the water disinfecting column 600 is in a form of a fixed-bed column, wherein the nanocomposites 608 are fixed in the internal cavity inside a column bed, and the contaminated water 610 is passed through the nanocomposites 608. In another embodiment, the water disinfecting column 600 is in a form of a fluidized-bed column, wherein the nanocomposites are floating in the internal cavity when the contaminated water 610 is passed through the nanocomposites. In another embodiment, the inlet 604 and the outlet 606 are substantially the same, wherein each is configured to load/unload a volumetric flow rate of up to 1,000 L/min, preferably 500 L/min to/from the vessel 602. The contaminated water 610 may be delivered to the vessel from a top of the vessel, as shown in FIG. 6, or from a bottom of the vessel, not shown. In view of that, in some embodiments, the inlet is located at the top of the vessel and the outlet is located at the bottom of the vessel, as shown in FIG. 6. Alternatively, the inlet may be located at the bottom of the vessel and the outlet may be located at the top of the vessel, not shown.

The examples below are intended to further illustrate protocols for the nanocomposite, the method of making the nanocomposite, and the method of disinfecting the aqueous solution with the nanocomposite, and are not intended to limit the scope of the claims.

Example 1—Materials, Synthesis, and Characterization

In the following examples one approach for making a nanocomposite of polypyrrole, AgNPs, and carbon nanotubes via in situ oxidative polymerization of pyrrole is provided. FIG. 1 shows the formation of the nanocomposite with different percentages of CNT.

Analytical grade pyrrole, silver nitrate, acetone, carbon nanotubes (CNT), i.e. single-walled carbon nanotubes, were purchased from Sigma-Aldrich and used as received. Aqueous solutions were prepared from distilled water. Different compositions of CNT were made according to the following procedure. In a conical flask containing 80 ml distilled water, 0.6 g (or 8.94 mmol) of pyrrole was added and stirred vigorously to get a clear solution. Then appropriate amount of CNT (0, 10, 20, 40, 60% w/w of pyrrole) was mixed with the pyrrole solution with stirring. An aqueous solution of silver nitrate (3.78 g, 22.25 mmol) in 20 ml distilled water was added in one portion to the above mixture and the reaction mixture was stirred at room temperature overnight and stored for a week in dark room. The resulting solids were filtered, rinsed with water for four times, rinsed with acetone for two times, and dried overnight in an oven at 50° C. The weights of the resulting solids were 3.01, 3.1, 3.21, 3.35, and 3.51 g corresponding to PPy/AgNPs, $CNT_{10}$/PPy/AgNPs, $CNT_{20}$/PPy/AgNPs, $CNT_{40}$/PPy/AgNPs, and $CNT_{60}$/PPy/AgNPs, respectively.

Infrared spectra were performed on a PerkinElmer spectrum 100 FT-IR spectrometer. All samples were prepared by mixing FTIR-grade KBr (Aldrich Chemicals) with 1.0 wt % of the sample and grinding to a fine powder. XRD patterns of the samples were recorded on a D8 Advanced diffractometer (Bruker AXS, Germany) with $CU_{K\alpha}$ radiation (1.54178 A°). The operation voltage and current were kept at 40 kV and 40 mA, respectively. The morphology and size of the nanoparticles were characterized at 100 kV by a JEOL 2010 TEM. Thermogravimetric analysis (TGA) was carried on a Shimadzu TGA-50H thermogravimetric analyzer and the samples were heated from room temperature to 900° C. with a ramp rate of 10° C./min in an inert nitrogen atmosphere.

*E. coli* and *S. aureus* were grown on a blood agar for one day at 36° C. The number of bacteria was determined by a bacterial counter. The grown bacteria were delivered directly to a column (1×1 cm i.d.) containing $CNT_{0-60}$/PPy/AgNPs (200 mg). The adsorbed bacteria were eluted with distilled water at a flow rate of 0.5 ml/min and 1 ml fractions were collected.

The statistical analyses were performed by a one-way ANOVA and the t-test. The results were expressed as means±S.D. Difference are considered significant when $P<0.05$.

Example 2—FTIR Spectra Analysis

Figure 2A:
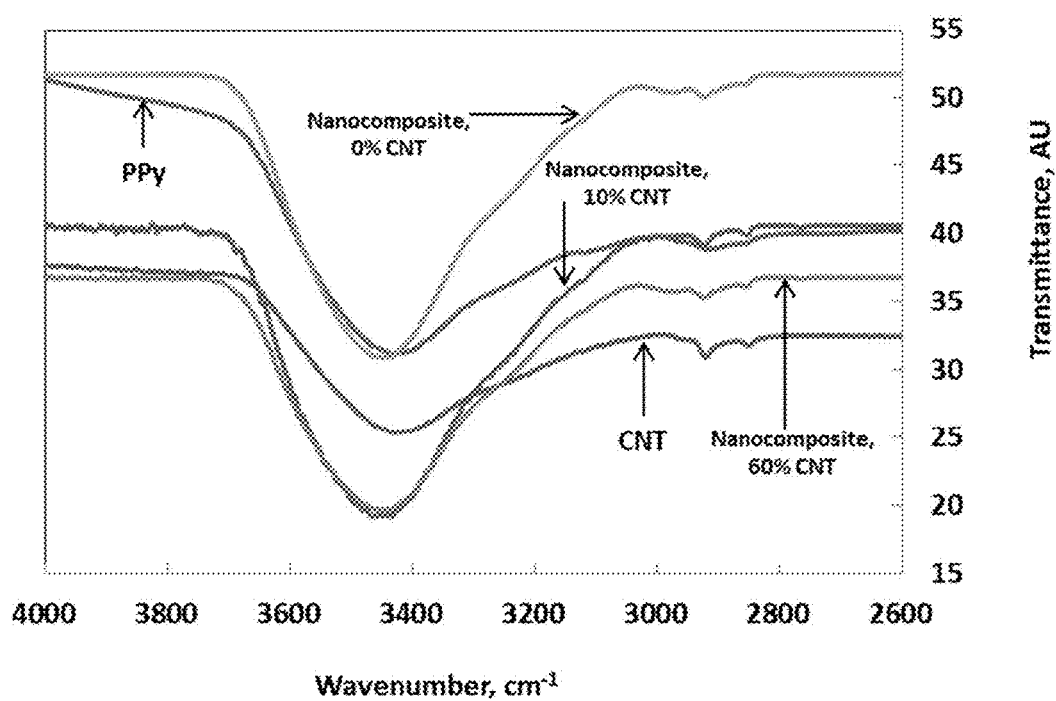
FIG. 2A represents FTIR spectra in a wavelength range of 2,600 to 4,000 $cm^{-1}$ of the PPy, the CNTs, the nanocomposite of PPy and AgNPs, the nanocomposite of PPy, AgNPs, and 10 wt % CNTs, and the nanocomposite of PPy, AgNPs, and 60 wt % CNTs, wherein the weight percent of CNT is relative to the weight of the PPy.
Figure 2B:
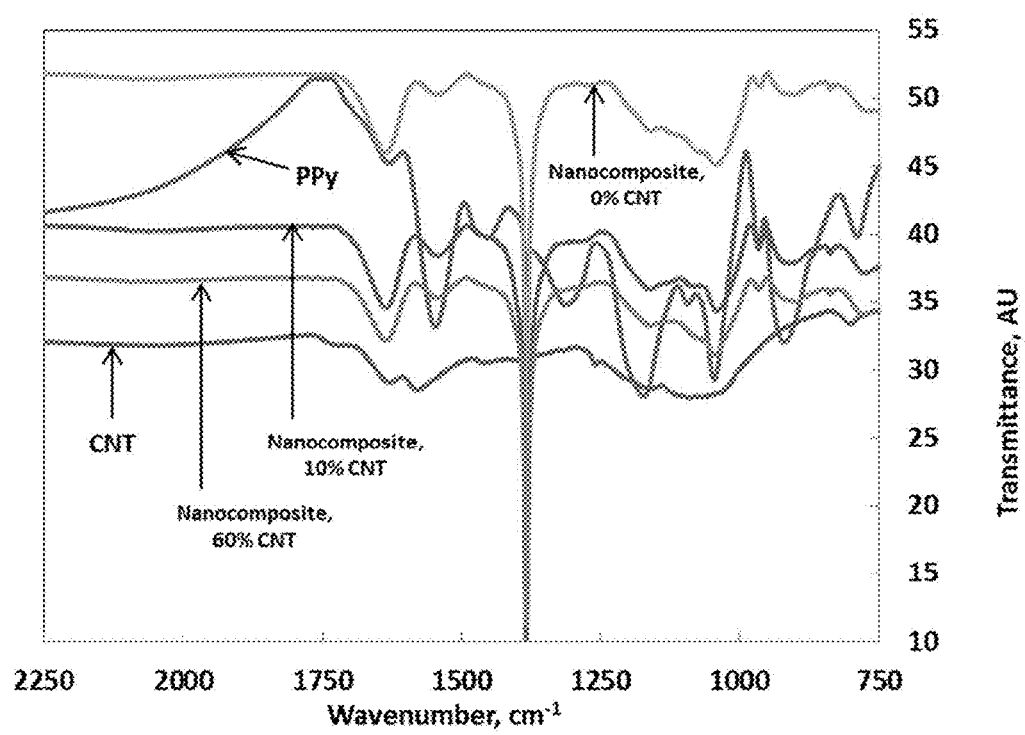
FIG. 2B represents FTIR spectra in a wavelength range of 750 to 2,250 $cm^{-1}$ of the PPy, the CNTs, the nanocomposite of PPy and AgNPs, the nanocomposite of PPy, AgNPs, and 10 wt % CNTs, and the nanocomposite of PPy, AgNPs, and 60 wt % CNTs, wherein the weight percent of CNT is relative to the weight of the PPy.

The FTIR spectra of all samples are shown in FIGS. 2A and 2B. A broad absorption band is shown in the range between 4000 and 2600 $cm^{-1}$ which could be attributed to O—H present in the samples and/or water, C—H and N—H groups. The absorption band around 1582 and 1630 $cm^{-1}$ in the CNT spectrum represents the C═C bond vibration [I. Montesa, E. Muñoz, A. M. Benito, W. K. Maser, M. T. Martinez, J. Nanosci. Nanotechnol., 2007, 7, 3473-3476]. Comparing the intensity of these two bands with the corresponding two bands present in composite samples indicates the overweight vibrations due to PPy to those resulted from CNT, as the intensity was in an opposite manner.

In addition, polypyrrole was separately formed by following the oxidative ferric chloride method reported in the literature [M. Omastová, M. Trchová, J. Kovářová, J. Stejskal, Synth. Met., 2003: 138, 447-455] so to compare its FTIR data with PPy made by in situ oxidative polymerization using silver nitrate as oxidant and in the presence of different percentages of CNT.

Interestingly, regardless the CNT content, PPy made in composite did not show the broad absorption band that observed above 2000 $cm^{-1}$ for the one made with $FeCl_3$, indicating the absence of intra-chain excitations due to the presence of AgNPs in the composite in core-shell forms. Additionally, PPy alone showed the characteristic peaks at 1632 $cm^{-1}$ (due to C═C and/or C═N bond), 1550 $cm^{-1}$ (likely due the skeletal vibrations involving C═C), 1454 $cm^{-1}$ (correspond to C—N stretching vibration), 1314 $cm^{-1}$ (due to C—H and/or C—N in-plane deformation), 1173 $cm^{-1}$ (due to a breathing vibration of the pyrrole ring), 1046 $cm^{-1}$ (due to C—H and/or C—N in-plane deformation, 922 $cm^{-1}$ (due to C—H out of plane deformation vibrations of the ring) and 790 $cm^{-1}$ (due to C—H out of plane ring deformation) [M. Omastová, M. Trchová, J. Kovářová, J. Stejskal, Synth. Met., 2003: 138, 447-455; E. J. Oh, K. S. Jang and A. G. MacDiarmid, Synth. Met., 2002, 125, 267-272; S. Ghosh, G. A. Bowmaker, R. P. Cooney and J. M. Seakins, Synth. Met., 1998, 95, 63-67]. These aforementioned peaks were either blue shifted from 1632 $cm^{-1}$ for PPy alone to 1637 $cm^{-1}$ for PPy in composites or red shifted for the rest of absorption bands together with the disappearance of the two peaks corresponding to those appeared at 1454 and 1314 $cm^{-1}$ in PPy alone, indicating the existence of interactions of PPy with composite components. A striking absorption peak situated at 1386 cm$^{-1}$ due to nitrate counter anions is a strong evident for the in situ oxidative polymerization of pyrrole with silver nitrate [M. Omastová, K. Mosnácková, P. Fedorko, M. Trchová and J. Stejskal, Synth. Met., 2013, 166, 57-62].

Example 3—XRD Analysis

The XRD patterns of the CNT, PPy, 0% CNT (i.e. PPy/AgNPs nanocomposite), and the nanocomposite with 60% CNT (i.e. CNT$_{60}$/PPy/AgNPs) are shown in FIGS. 3A, 3B, 3C, and 3D. The XRD pattern of pristine CNT shows the peak at 26° correspond to (0 0 2) plane of graphite (JCPDS card no. 75-1621). Meanwhile, the XRD of the PPy shows the broad peaks around 2θ 20-42° indicating the presence of the PPy in an amorphous form [L. J. Buckley, D. K. Roylance and G. E. Wnek. J. Polym. Sci., part B, Polym. Phys., 1987, 25, 2179-2188]. The XRD pattern of 0% CNT (i.e. PPy/AgNPs nanocomposite) showed the typical diffraction peaks of silver nanoparticles at 2θ=38.2, 44.4, 64.5, 77.5°, corresponding to the cubic, crystalline structure of silver and are assigned to (111), (200), (220) and (311) planes of silver respectively, [JCPDS No 03-0931], [S. S. Sana, V. R. Badinni, S. K. Arala and V. K. N. Boya, Mater. Lett., 2015, 145, 347-350] and broad peak in the region 20° to 42° due to the amorphous structure of polypyrrole was observed. The XRD pattern of 60% CNT (i.e. CNT$_{60}$/PPy/AgNPs) showed the typical diffraction peaks of silver nanoparticles at 2θ=38.2, 44.4, 64.5, 77.5°, corresponding to the cubic, crystalline structure of silver and are assigned to (111), (200), (220) and (311) planes of silver respectively [JCPDS No 03-0931], [S. S. Sana, V. R. Badinni, S. K. Arala and V. K. N. Boya, Mater. Lett., 2015, 145, 347-350] and broad peak in the region 20° to 42° due to the amorphous structure of polypyrrole was observed indicating a homogeneous involvement of polypyrrole with the AgNPs within the nanocomposite. The XRD pattern of 60% CNT (CNT$_{60}$/PPy/AgNPs) showed the characteristic diffraction peaks of silver nanoparticles in addition to much broad peak in the region 20° to 42° due to the presence of both CNT and amorphous polypyrrole was observed indicating a homogeneous dispersion of SWCNT in the composite.

Example 4—TEM

It was shown that the oxidative polymerization of pyrrole using silver nitrate as oxidant and pyrrole as reductant resulted in the formation of PPy/AgNPs nanocomposites. The morphology and particle sizes of CNT$_{0-60}$/PPy/AgNPs are shown in FIGS. 4A, 4B, 4C, 4D, 4E, and 4F. It is generally observed that AgNPs appear as dark spots and are coated by the PPy matrix shown in gray. Also, TEM images show that the PPy/AgNPs nanocomposite has a different morphology from those samples that contain SWCNTs. As the percentage of CNTs increases the morphology tends to become cylindrical due to the growing layers of the PPy onto the CNTs. This result can be explained based on the nucleation sites present in the amorphous layer of CNTs. Accordingly, the PPy is coated on the CNTs while AgNPs are simultaneously produced thereby forming a core-shell structure, wherein AgNPs are coated with a shell that contains CNTs and PPy.

Example 5—Thermal Analysis

The thermal stability of polymeric nanocomposite materials is affected by the presence of CNTs content. Therefore, it was necessary to reveal such effect and to see whether the results obtained above in TEM images in which the nanocomposites became more intimate with cylindrical morphology (60% CNT) would be reflected by its thermal stability compared with another lower content (10% CNT) and PPy/AgNPs.

Figure 5:
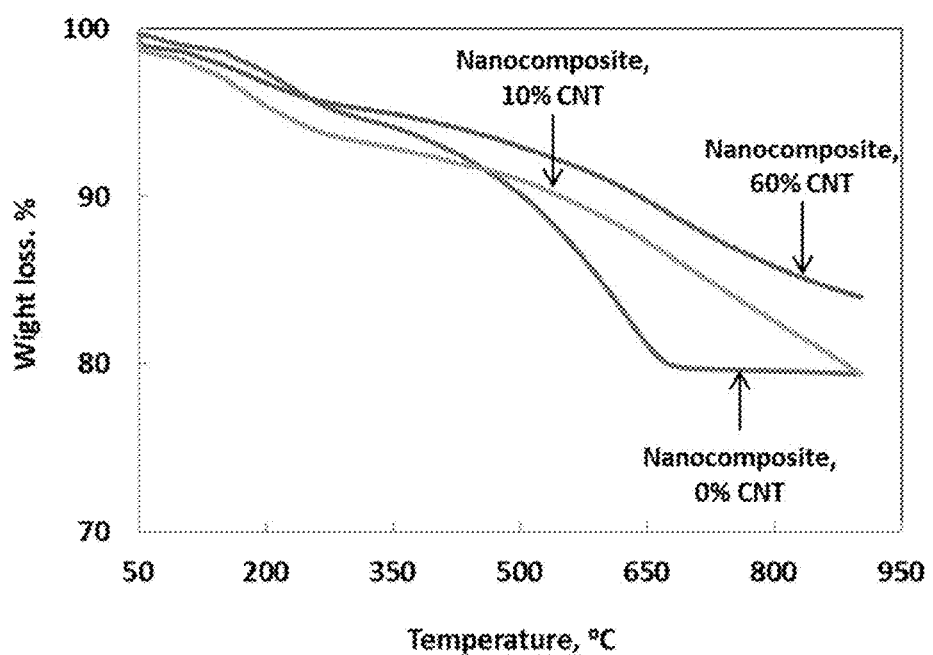
FIG. 5 represents thermogravimetric results of the nanocomposite of PPy and AgNPs, the nanocomposite of PPy, AgNPs, and 10 wt % CNTs, and the nanocomposite of PPy, AgNPs, and 60 wt % CNTs, wherein the weight percent of CNT is relative to the weight of the PPy.

FIG. 5 shows the TGA of the nanocomposites in absence of CNTs and in presence of different CNT percentages. The thermal stability of zero % CNTs sample (PPy/AgNPs) revealed a small fraction of weight loss up to 120° C. due to evaporation of adsorbed water, and weight loss from 150 to 263° C. attributed to the degradation of small chains of polypyrrole. Generally, the weight loss below 400° C. in the presence of CNT could be due to the decomposition of PPy oligomers, which may be trapped inside CNTs. For the temperatures above 400° C., however, the stability is higher in the presence of CNT than its absence as a consequence of coiling CNT with PPy and AgNPs. Then a significant weight loss takes place from 400 to 674° C. due to the complete degradation of polypyrrole. At this temperature (674° C.), the weight percentage of silver in the PPy/AgNPs nanocomposite was found to be about 80 wt % relative to the total weight of the nanocomposite. The thermal stability of other nanocomposites containing 10 and 60% was generally better than that of PPy/AgNPs nanocomposite. This stabilization is an indicative of CNT-PPy interactions [D. N. Huyen, N. T. Tung, T. D. Vinh and N. D. Thien, Sensors, 2012, 12, 7965-7974; B. Zhang, Y. Xu, Y. Zheng, L. Dai, M. Zhang, J. Yang, Y. Chen, X. Chen and J. Zhou, Nanoscale Research Letters, 2011, 6, 431-439]. It is worth mentioning that the silver content as well as the thermal stability for the PPy/AgNPs nanocomposite is higher than the previously reported nanocomposite materials [P. Dallas, D. Niarchos, D. Vrbanic, N. Boukos, S. Pejovnik, C. Trapalis and D. Petridis, Polymer, 2007, 48, 2007-2013].

Example 6—Bacterial Removal Process

Literature data indicate that both AgNPs and polypyrrole alone or in composite form have antimicrobial properties [R. M. El-Shishtawy, A. M. Asiri, N. A. M. Abdelwahed and M. M. Al-Otaibi, Cellulose, 2011, 18, 75-82; J. Upadhyay, A. Kumar, B. Gogoi and A. K. Buragohain, Materials Science and Engineering: C., 2015, 54, 8-13]. AgNPs attack bacterial cell membranes and kill the bacteria cells [S. C. Smith and D. F. Rodrigues, Carbon, 2015, 91, 122-143]. Polypyrrole molecules with positive charges adhere to the negatively charged bacteria cell membranes thereby inhibiting microbial growth [S. Ghosh, G. A. Bowmaker, R. P. Cooney and J. M. Seakins, Synth. Met., 1998, 95, 63-67]. On the other hand, CNTs possess excellent bacterial inactivation efficiency due to their large surface areas [S. C. Smith and D. F. Rodrigues, Carbon, 2015, 91, 122-143]. Previous studies indicated that batch disinfection of *E. coli* (gram-negative) were in the order SWCNTs-Ag(70.24%)>SWCNTs (38.89%), and for *S. aureus* (gram-positive) were in the order SWCNTs-Ag(95.79%)>SWCNTs(−131.40%). The negative number indicted that SWCNTs does not have antibacterial properties by itself, since the reproduction rate of *S. aureus* was higher than the disinfection rate. However, SWCNTs-Ag nanocomposite was found effective disinfectant against *S. aureus* compared to *E. coli* due to the higher affinity of SWCNTs to *S. aureus* colonies, when brought in close proximity with AgNPs. The effect of CNTs content in PPy/AgNPs nanocomposites is described here. The different disinfectant behavior of SWCNTs from being active (38.89%) for *E. coli* and inactive (−131.40%) for *S. aureus* was attributed to the difference in cell wall between *E. coli* (slim) and *S. aureus* (deep) [Y. N. Chang, J. L. Gong, G. M. Zeng, X. M. Ou, B. Song, M. Guo, J. Zhang and H.-Y. Liu, Process Safety and Environmental Protection, 2 0 1 6, 102, 596-605].

A filter column method was used to evaluate the performance of the nanocomposite for disinfecting contaminated water. Accordingly, a filter column for water disinfection was used, as shown in FIG. 6. The elution profiles of *E. coli* on $CNT_{0-60}$/PPy/AgNPs columns are summarized in Table 1. Twenty thousand bacteria were eluted with columns. For $CNT_{0-20}$/PPy/AgNPs columns, the number of eluted bacteria was increased with elution of water and decreased in fractions 4 and 5. The percent of adsorbed bacteria ranges from 87.5% to 95%. Approximately all bacteria were adsorbed by columns containing $CNT_{40-60}$/PPy/AgNPs nanocomposites. It appeared that the content of CNT in the nanocomposite determines the antibacterial performance with respect to *E. coli*. The nanocomposites with CNTs content of 40% or more revealed a complete removal (approximately 100% removal) of *E. coli*. The results are in a good agreement with previous studies [S. C. Smith and D. F. Rodrigues, Carbon, 2015, 91, 122-143].

TABLE 1

A typical elution profile for the chromatography of *E. coli* on different columns of CNT0-60/PPy/AgNPs.

| Sample | Number of bacteria eluted | | | | |
|---|---|---|---|---|---|
| | Fraction 1 | Fraction 2 | Fraction 3 | Fraction 4 | Fraction 5 |
| $CNT_0$/PPy/AgNPs | 0 | 290 ± 3.2 | 310 ± 5.2 | 134 ± 2.2 | 110 ± 2.2 |
| $CNT_{10}$/PPy/AgNPs | 0 | 120 ± 2.9 | 252 ± 4.8 | 230 ± 3.1 | 200 ± 3.5 |
| $CNT_{20}$/PPy/AgNPs | 0 | 193 ± 4.2 | 259 ± 3.6 | 270 ± 4.2 | 150 ± 3.8 |
| $CNT_{40}$/PPy/AgNPs | 0 | 1 ± 0.02 | 5 ± 0.03 | 3 ± 0.01 | 0 |
| $CNT_{60}$/PPy/AgNPs | 0 | 0 | 0 | 0 | 0 |

The number of bacteria (*E. coli*) loaded into column is 20,000.
Values are presented as means ± SD (n = 3).

Figure 7:
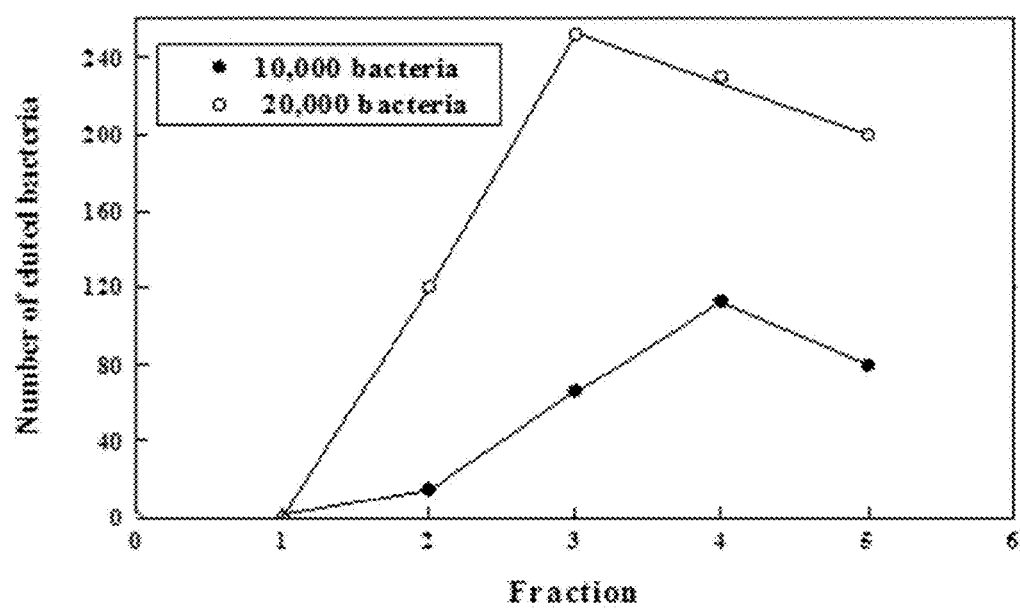
FIG. 7 represents a comparison of the number of eluted bacteria when two contaminated water samples at different bacteria concentrations are contacted with the nanocomposite.

To further elaborate the antimicrobial effect, a lower load of *E. coli* (ten thousand) was applied into $CNT_{10}$/PPy/AgNPs column. FIG. 7 shows comparative elution between high and low bacterial inclusions. It was observed that the elution of bacteria increased with increasing the inclusion of bacteria until the number of bacteria reaches 240. The elution of bacteria declined afterwards, in a comparative manner. From these results one can conclude that the increase of the number of bacteria may be attributed to the overload of the bacteria and the flow rate of the column and during the time of elution the most of bacteria get adsorbed. Interestingly, *S. aureus* was completely adsorbed by $CNT_{0-60}$/PPy/AgNPs columns indicating that PPy/AgNPs obtained in this work is specific for excellent removal of *S. aureus* (100%). On the other hand, the $CNT_{60}$/PPy/AgNPs nanocomposite was found to be effective towards *E. coli* with complete removal (100%) indicating an existence of synergistic effect in this nanocomposite.

The invention claimed is:

1. A nanocomposite, comprising:
   a core and a shell that covers at least a portion of the core,
   wherein the core comprises silver nanoparticles having an average diameter in a range of 20 to 50 nm, and the shell comprises polypyrrole,
   wherein an amount of polypyrrole in the nanocomposite is in the range of 5 to 25 wt %, and an amount of silver nanoparticles in the nanocomposite is in the range of 60 to 90 wt %, each relative to a total weight of the nanocomposite,
   wherein the shell covers at least 60% but no more than 85% of an external surface area of the core, and
   wherein the shell has a thickness in the range of 100 to 250 nm.

2. The nanocomposite of claim 1, wherein the shell further comprises carbon nanotubes that are dispersed in the polypyrrole.

3. The nanocomposite of claim 2, wherein a weight ratio of the carbon nanotubes to the polypyrrole is in the range of 1:20 to 5:1.

4. The nanocomposite of claim 2, wherein the carbon nanotubes are single-walled carbon nanotubes with an average diameter in the range of 1 to 20 nm.

5. The nanocomposite of claim 2, wherein the carbon nanotubes are multi-walled carbon nanotubes with an outer diameter in the range of 30 to 100 nm.

6. A method of making a nanocomposite, comprising:
   mixing pyrrole with water and stirring to form a first mixture;
   mixing a silver-containing solution with the first mixture and stirring for up to 30 hours to form a second mixture, wherein the pyrrole coordinates with silver ions present in the silver-containing solution; and
   storing the second mixture, thereby reducing the silver ions to silver nanoparticles while concurrently oxidizing the pyrrole to form polypyrrole via an oxidative polymerization, thereby forming the nanocomposite comprising:
   a core and a shell that covers at least a portion of the core,
   wherein the core comprises silver nanoparticles having an average diameter in a range of 20 to 50 nm, and the shell comprises polypyrrole,
   wherein an amount of polypyrrole in the nanocomposite is in the range of 5 to 25 wt %, and an amount of silver nanoparticles in the nanocomposite is in the range of 60 to 90 wt %, each relative to a total weight of the nanocomposite,
   wherein the shell covers at least 60% but no more than 85% of an external surface area of the core, and
   wherein the shell has a thickness in the range of 100 to 250 nm.

7. The method of claim 6, wherein the first mixture is stirred at a temperature of 15 to 35° C., and wherein the second mixture is stored at a temperature of 15 to 35° C. for up to 10 days at an illuminance of no more than 50 lux.

8. The method of claim 6, wherein the silver-containing solution is an aqueous silver nitrate solution, and wherein a molar ratio of the pyrrole to silver nitrate is in the range of 1:1 to 1:5.

9. The method of claim 6, further comprising:
   mixing a carbon nanotube suspension with the first mixture and sonicating prior to mixing the silver-containing solution with the first mixture, to form a nanocomposite having a core comprising silver nanoparticles and a shell comprising polypyrrole and carbon nanotubes.

10. The method of claim 9, wherein a weight ratio of the carbon nanotubes to the pyrrole is in the range of 1:20 to 5:1.

11. The method of claim 9, wherein the carbon nanotubes are single-walled carbon nanotubes with an average diameter in the range of 1 to 20 nm.

12. A method of disinfecting an aqueous solution comprising *Staphylococcus aureus*, the method comprising:
    contacting the aqueous solution with the nanocomposite of claim 1 to remove at least a portion of *Staphylococcus aureus*, wherein no more than 50 milliliters of the aqueous solution is contacted per one gram of the nanocomposite.

13. The method of claim 12, wherein a ratio of a number of viable *Staphylococcus aureus* cells per one milliliter of the aqueous solution after the contacting to the number of viable *Staphylococcus aureus* cells per one milliliter of the aqueous solution before the contacting is in the range of 1:5 to 1:10,000.

14. A method of disinfecting an aqueous solution comprising *Escherichia coli* cells, the method comprising:
    contacting the aqueous solution with the nanocomposite of claim 2 to remove at least a portion of *Escherichia coli* cells, wherein no more than 50 milliliters of the aqueous solution is contacted per one gram of the nanocomposite.

15. The method of claim 14, wherein a ratio of a number of viable *Escherichia coli* cells per one milliliter of the aqueous solution after the contacting to the number of viable *Escherichia coli* cells per one milliliter of the aqueous solution before the contacting is in the range of 1:5 to 1:100.

16. The method of claim 14, wherein a weight ratio of carbon nanotubes to the polypyrrole in the nanocomposite is in the range of 1:10 to 1:1, and wherein a ratio of a number of viable *Escherichia coli* cells per one milliliter of the aqueous solution after the contacting to the number of viable *Escherichia coli* cells per one milliliter of the aqueous solution before the contacting is in the range of 1:100 to 1:10,000.

17. The method of claim 14, wherein the aqueous solution further comprises one or more bacteria selected from the group consisting of *Klebsiella pneumonia, Chlamydia trachomatis, Neisseria gonorrhoeae, Yersinia pestis, Clostridium tetani, Providencia stuartii*, Pneumobacillus, *Vibrio vulnificus, Candida albicans, Bacillus cloacae, Pseudomonas maltophila, Pseudomonas aeruginosa, Streptococcus hemolyticus* B, *Citrobacter*, and *Salmonella paratyphi* C, and wherein a ratio of a number of viable *Escherichia coli* cells and the one or more bacteria cells per one milliliter of the aqueous solution after the contacting to the number of viable *Escherichia coli* cells and the one or more bacteria cells per one milliliter of the aqueous solution before the contacting is in the range of 1:2 to 1:100.

18. The nanocomposite of claim 3, wherein a weight ratio of the carbon nanotubes to the polypyrrole is in the range of 1:5 to 1:1.5.

19. The nanocomposite of claim 18, wherein at least 70% but no more than 90% of an external surface area of the carbon nanotubes are covered with the polypyrrole.

* * * * *